US007294462B2

(12) United States Patent
Nasu et al.

(10) Patent No.: US 7,294,462 B2
(45) Date of Patent: Nov. 13, 2007

(54) METHOD FOR DETECTION OF BASE SEQUENCE OF INTEREST

(75) Inventors: Hisanori Nasu, Yokohama (JP); Hiroaki Ono, Yokohama (JP); Akito Mugita, Yokohama (JP); Ichiro Nakayama, Kawasaki (JP); Takanori Kobayashi, Yokohama (JP); Tetsuji Masaoka, Watarai-gun (JP); Satoru Kuhara, Fukuoka (JP); Yoshizumi Ishino, Fukuoka (JP)

(73) Assignee: Japan Software Management Co., Ltd., Kanagawa-ken (JP)

( * ) Notice: Subject to any disclaimer, the term of this patent is extended or adjusted under 35 U.S.C. 154(b) by 447 days.

(21) Appl. No.: 10/802,055

(22) Filed: Mar. 17, 2004

(65) Prior Publication Data

US 2005/0208502 A1 Sep. 22, 2005

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.4
(58) Field of Classification Search .............. 435/6; 536/23.1, 24.3
See application file for complete search history.

(56) References Cited

U.S. PATENT DOCUMENTS 5,741,644 A * 4/1998 Kambara et al. ............ 435/6
5,935,794 A * 8/1999 Kambara et al. ............ 435/6
5,962,223 A 10/1999 Whiteley et al.
6,228,580 B1 5/2001 Blumenfeld et al.
2004/0248136 A1* 12/2004 Yoshizaki et al. .......... 435/6

FOREIGN PATENT DOCUMENTS

| EP | 1 164 201 A1 | 12/2001 |
| WO | WO 99/28494 A1 | 6/1999 |
| WO | WO 00/68421 A2 | 11/2000 |
| WO | WO 2004/015080 A2 | 2/2004 |

OTHER PUBLICATIONS

Veerle A.M.C. Somers, et al. "A rapid, reliable method for detection of known point mutations: Point-EXACCT", *Nucleic-Acids Research*, vol. 22, No. 22, Nov. 11, 1994, pp. 4840-4841, XP002013669.
European Search Report.
Mark Schena, et al. "Quantitative Monitoring of Gene Expression Patterns with a Complementary DNA Microarray" *Science*, vol. 270, pp. 467-470, Oct. 20, 1995.

* cited by examiner

*Primary Examiner*—Ethan Whisenant
(74) *Attorney, Agent, or Firm*—Sughrue Mion, PLLC

(57) ABSTRACT

There is provided a method for the detection of a base sequence of interest when amount of a sample DNA or RNA is little and plural base sequences of interest to be detected are present in the sample DNA or RNA.

The Problem is solved by a method for the detection of an base sequence of interest in a sample DNA or RNA comprising the steps of (1) contacting a sample DNA or RNA to a probe DNAs or RNAs in an aqueous solution to form a hybridization complex; (2) isolating the hybridization complex; (3) dissociating the complex to recover the probe DNAs or RNAs; and (4) identifying the said probe DNAs or RNAs to detect an base sequence of interest in the sample DNA or RNA.

8 Claims, 3 Drawing Sheets

METHOD FOR DETECTION OF BASE SEQUENCE OF INTEREST

BACKGROUND OF THE INVENTION

The present invention relates to a method for detecting whether base sequences of interest are present in a sample DNA or RNA utilizing a bonding of a sample DNA or RNA with probe DNAs or RNAs by means of hybridization. The case wherein a sample or probes are DNA can be considered in a similar way to the case wherein a sample or probes are RNA. Accordingly, the case wherein both of a sample and probes are DNA is described hereinafter as an example.

A conventional means for detecting whether a base sequence of interest is present in a sample DNA is carried out as follows: DNA having a base sequence complementary to a sample DNA of interest to be detected is prepared as a probe DNA and made into a DNA chip by immobilizing it on glass or membrane. The sample DNA is hybridized with the probe DNA immobilized on a DNA chip. When the intended sequence is present in the sample DNA, a site having the base sequence of interest in the sample DNA is bonded to the probe DNA immobilized on the DNA chip to form a hybridization complex. When there is no base sequence of interest in sample DNA, there is no bonding of sample DNA to the probe DNA and, therefore, sample DNA remains in a solution. When the DNA chip is washed after the hybridization, the DNA in solution is removed while bonded sample DNA is not removed. A method for the detection of a probe DNA forming a hybridization complex is effected as follows: The sample DNA which has been previously labeled by a fluorescent substance is radiated by exciting with a light source such as lamp or laser. The formed image is read by an DNA chip reading device to determine whether the base sequence of interest is present in a sample DNA which is hybridized with probe (Science, 270:467-470).

FIG. 2 is an example of a method for the detection of an base sequence of interest using a DNA chip which has been often utilized recently. This example shows a means for the detection whether four different base sequences of interest, i.e. a base sequence of interest (1) 1, a base sequence of interest (2) 2, a base sequence of interest (3) 3 and a base sequence of interest (4) 4 are present in a sample DNA 5. In this example, the base sequence of interest (1) 1 and the base sequence of interest (4) 4 are present in a sample DNA.

FIG. 2(A) is a sample DNA 5 which is previously subjected to a fluorescence labeling and in which the base sequence of interest (1) 1 and the base sequence of interest (4) 4 are present.

FIG. 2(B) is a DNA group 14 comprising DNA 1a of the base sequence of interest (1) and DNA 1b complementary to DNA 1a, DNA 2a of the base sequence of interest (2) and DNA 2b complementary to DNA 2a, DNA 3a of the base sequence of interest (3) and DNA 3b complementary to DNA 3a and DNA 4a of the base sequence of interest (4) and DNA 4b complementary to DNA 4a.

In FIG. 2(C), complementary chain DNAs 1b to 4b from FIG. 2(B) are immobilized on glass or membrane as a probe DNA group 8 to prepare a DNA chip 9 of FIG. 2(D).

In FIG. 2(E), a sample DNA 5 and a probe DNA group 8 immobilized on the DNA chip 9 are placed into a hybridization solution 10 for hybridization. The site of the base sequence of interest (1) 1 in a sample DNA 5 and the DNA 1b of the base sequence of interest (1) are in a relation of complementary chain and, therefore, the site of the base sequence of interest (1) 1 in the sample DNA 5 and the complementary chain DNA 1b are hybridized and bonded.

FIG. 2(F) shows a reading means of DNA chip 9 after the hybridization in which the fluorescence label 6 is emitted by exciting with a lamp 11 and read by a DNA chip reading device 7. In this example, the position of the complementary DNA 1b of the base sequence of interest (1) 1 bonded by means of hybridization complex formation to the site of the base sequence of interest (1) 1 in the sample DNA 5 shines.

FIG. 2(G) is an image 12 read by the DNA chip reading device 7 and, from the shining position, it is found that the base sequence of interest (1) 1 is present in the sample DNA 5. At present, it is detected whether the base sequence of interest is present in a sample DNA by such means.

According to the conventional method, when the amount of a sample DNA is small, only a hybridization of one sample DNA with one probe DNA is possible since the probe DNA is immobilized on glass or membrane. Therefore, there is a problem that, when there are plural kinds of base sequences of interest to be detected in a sample DNA, only one of them is bonded to sample DNA while other base sequences of interest cannot be detected. Accordingly, a sample DNA must be amplified and increased. However, there is a problem that, when the sample DNA is an unknown DNA, sizes of the molecule are various, etc., the condition for the amplification is difficult. In the case of hybridization using a DNA chip, the space where the hybridization is carried out is too large and, therefore, there is a problem that probability to encounter the immobilized probe DNA and a sample DNA is low. In addition, molecular weight of the sample DNA is greatly different from that of the probe DNA and, therefore, there is a problem that it is difficult to set up experimental conditions such as temperature which is a condition for the hybridization.

The present invention has been carried out in view of the problems in the prior art as such. It is an object of the present invention to make hybridization of plural probe DNAs or RNAs with a sample DNA or RNA possible even when the amount of sample DNA or RNA is little and to provide a method where, even when plural kinds of base sequences of interest are present in a sample DNA or RNA, they can be easily detected.

SUMMARY OF THE INVENTION

The present invention is related to a method for detecting base sequences of interest in a sample DNA or RNA comprising the steps of:

(1) contacting a sample DNA or RNA with probe DNAs or RNAs in an aqueous solution to form a hybridization complex complex;

(2) isolating the hybridization complex;

(3) dissociating the hybridization complex to recover the probe DNAs or RNAs; and (4) identifying the said probe DNA or RNA to detect an base sequence of interest in the sample DNA or RNA.

The present invention can be applied to four cases:
(i) when sample is DNA and probe is DNA; (ii)when sample is RNA and probe is RNA; (iii)when sample is DNA and probe is RNA; and (iv) when sample is RNA and probe is DNA. The case in which sample or probe is DNA can be considered in a similar way to the case in which sample or probe is RNA. Accordingly, the case wherein both of sample and probe are DNA are described hereinafter.

In the present invention, a probe DNA which is immobilized on glass or membrane in a conventional method is not immobilized. An aqueous solution of a sample DNA and that of a probe DNA are prepared and both aqueous solutions are mixed under a hybridization condition to form a hybridization complex. As a result thereof, it is now possible that plural kinds of probe DNAs are hybridized with a sample DNA even when the amount of sample DNA is little. After that, a hybridization complex is isolated, the probe DNA is then recovered from the hybridization complex and the probe DNA is identified to detect the base sequence of interest in the sample DNA.

Thus, a sample DNA and probe DNAs are hybridized in a tube. The space for the hybridization can be made small and possibility of the sample DNA to encounter the probe DNAs can be made high. In addition, as a result of hybridization in a tube, the sample DNA can be detected even when its amount is small. Further, plural probe DNAs can be used for hybridization with one sample DNA.

Identification of the isolated probe DNA can be carried out in such a manner that c-probe DNA complementary to the probe DNA is prepared and is hybridized with the probe DNA. Thus, when c-probe DNAs complementary to the probe DNAs are immobilized on glass, membrane or the like to form a c-probe DNA chip, it is hybridized with a probe DNA to identify the probe DNAs. Since molecular weight of the probe DNA and that of c-probe DNA on the c-DNA chip are nearly same, they can easily bond to form a hybridization complex. When the probe DNA is labeled with fluorescent substance and the c-DNA chip hybridized with it is read by a DNA chip reading device, the place where the probe DNA is bonded to the c-probe DNA shines and, from its position on the c-DNA chip, it is now possible to identify the probe DNA. Thus, it is noted that a base sequence of the c-probe DNA bonded to the probe DNA is the base sequence of interest existing in the sample DNA.

To sum up, in the conventional art, a hybridization is for one sample DNA to one probe DNA but, according to the present invention, it is now possible plural probe DNAs are hybridized to one sample DNA and the probe DNA bonded to the sample DNA by hybridization can be detected by a c-probe DNA complementary to the probe DNA. When reading of the c-DNA chip is carried out by means of light, it is necessary to label the probe DNA with fluorescent substance before the hybridization of the isolated probe DNA with c-probe DNA. The labeling of probe DNA is well known to those skilled in the art (Nucleic Acids Research, 13:2399-2412; DNA Sequence 4:135-141). Oligonucleotide having various fluorescent substance can be synthesized using a commercially available DNA synthesizer.

BRIEF DESCRIPTION OF THE DRAWINGS

In FIG. 1 and FIG. 2, 1 is a base sequence of interest (1); 1a is a DNA of the base sequence of interest (1); 1b is a complementary chain DNA of the base sequence of interest (1); 2 is a base sequence of interest (2); 2a is a DNA of the base sequence of interest (2); 2b is a complementary chain DNA of the base sequence of interest (2); 3 is a base sequence of interest (3); 3a is a DNA of the base sequence of interest (3); 3b is a complementary chain DNA of the base sequence of interest (3); 4 is a base sequence of interest (4); 4a is a DNA of the base sequence of interest (4); 4b is a complementary chain DNA of the base sequence of interest (4); 5 is a sample DNA; 6 is a fluorescence label; 7 is a DNA chip reading device; 8 is a probe DNA group; 9 is a DNA chip; 10 is a hybridization solution; 11 is a lamp; 12 is a read image; 13 is glass; 14 is a DNA group; 15 is a c-probe DNA group; 16 is a c-DNA chip; 17 is a magnetic bead; and 18 is a magnet.

DETAILED DESCRIPTION OF THE PREFERRED EMBODIMENTS

Figure 1:
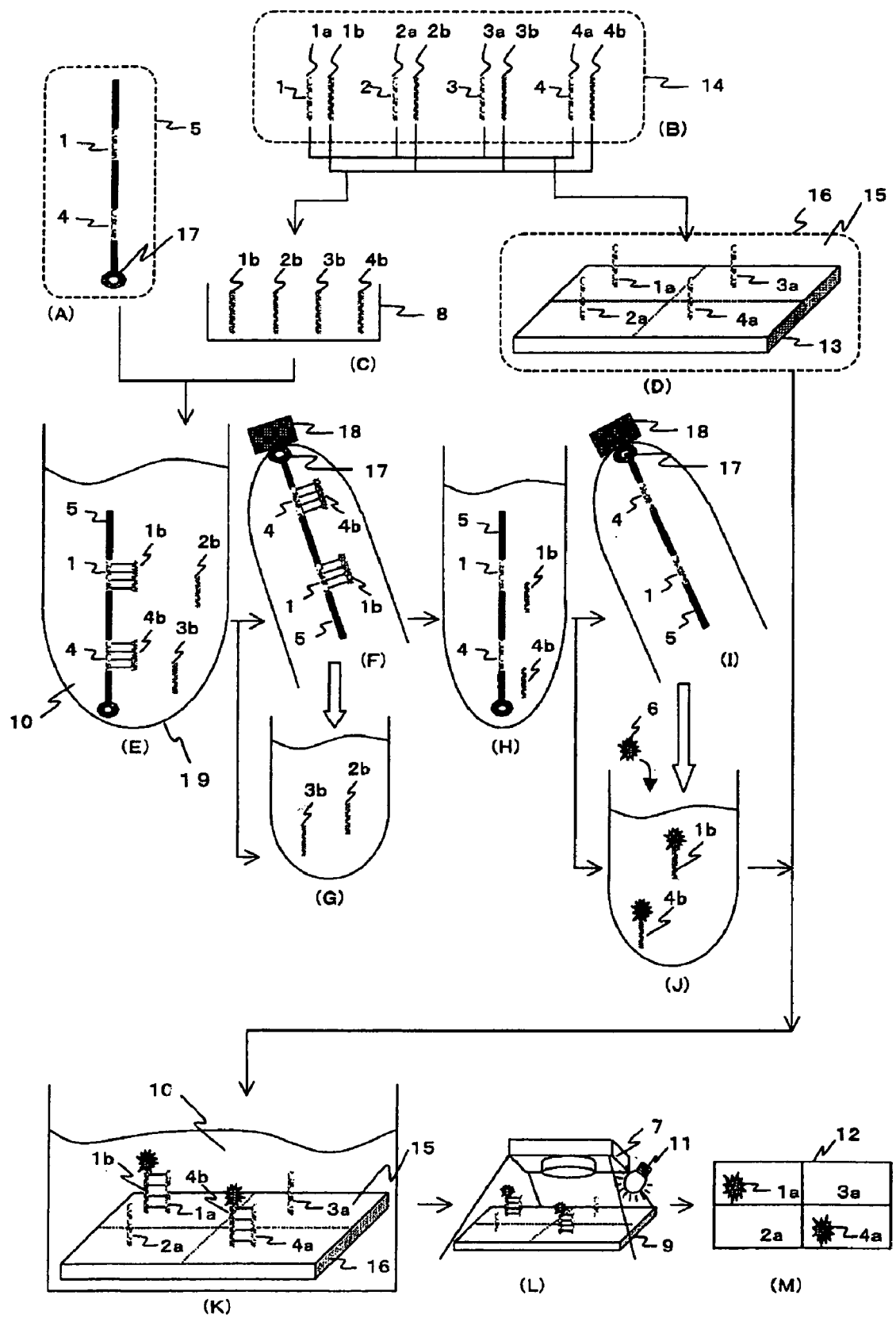
FIG. 1 is drawings which illustrate a principle of the present invention and represent a detecting means whether a base sequence of interest is present in a sample DNA.
Figure 2:
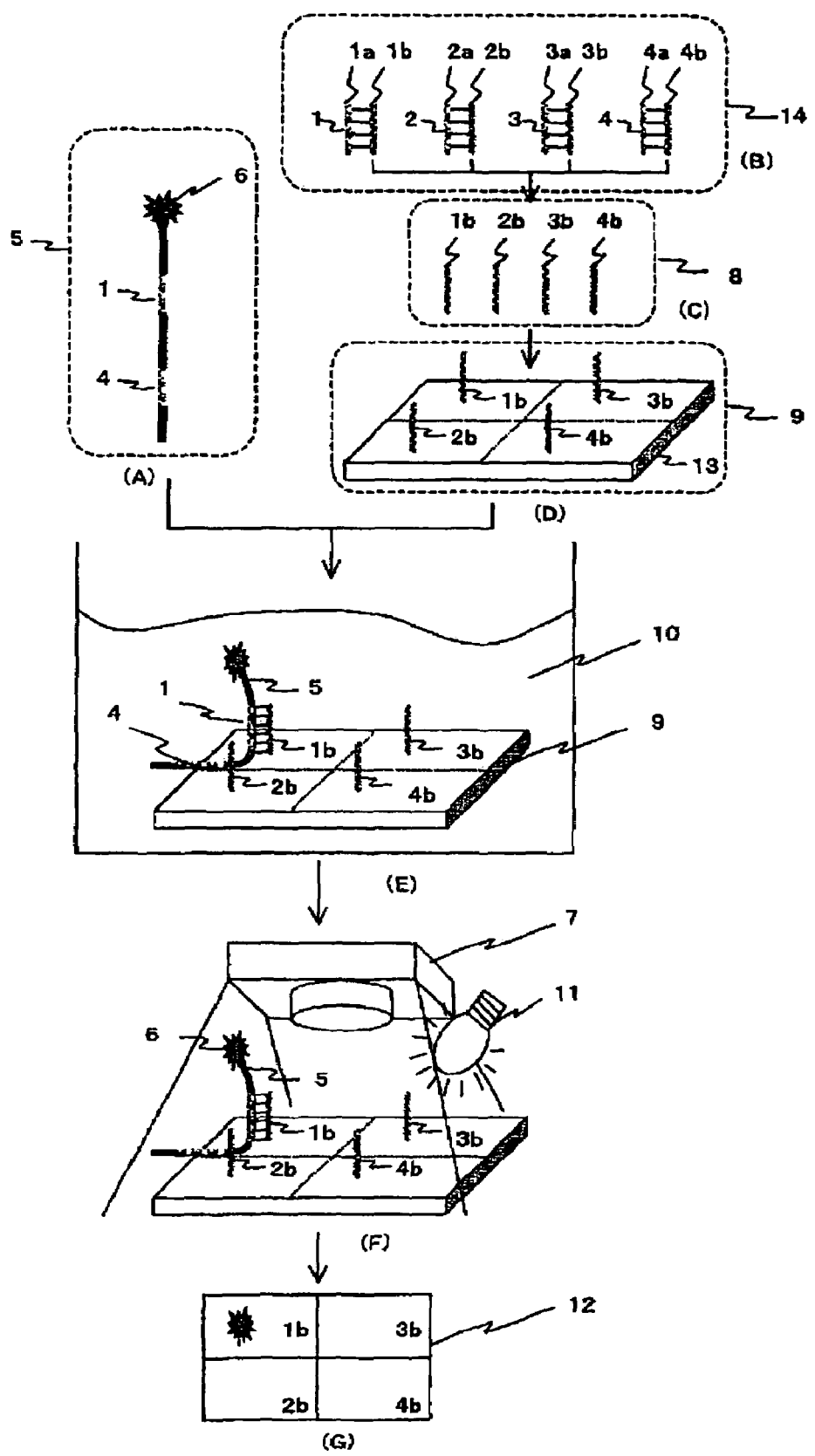
FIG. 2 is drawings which illustrate an example of method for the detection of a base sequence of interest using a DNA chip which is often utilized recently.

As hereunder, an embodiment of the present invention will be illustrated by referring to drawing. FIG. 1 is drawings which illustrate a principle of the present invention and a detecting means whether a base sequence of interest is present in a sample DNA.

In this example, a method of detection of base sequence of interest is shown, using an example where there are four base sequences of interest (1) to (4) and two base sequences of interest (1) and (4) among them are present in a sample DNA 5.

FIG. 1(A) is a sample DNA 5 which is a detection object where the base sequence of interest (1) 1 and the base sequence of interest (4) 4 are present. A magnetic bead 17 for controlling the sample DNA 5 is bonded to a sample DNA.

FIG. 1(B) is a pair of DNA group 14 for detecting the base sequence of interest and consists of DNA 1a of a base sequence of interest (1) and a complementary chain DNA 1b of a base sequence of interest (1), DNA 2a of a base sequence of interest (2) and a complementary chain DNA 2b of a base sequence of interest (2), DNA 3a of a base sequence of interest (3) and a complementary chain DNA 3b of a base sequence of interest (3) and DNA 4a of a base sequence of interest (4) and a complementary chain DNA 4b of a base sequence of interest (4).

FIG. 1(C) is a probe DNA group 8 used for hybridizing with and detecting a sample DNA, and consists of DNA 1b of a base sequence of interest (1) 1, DNA 2b of a base sequence of interest (2) 2, DNA 3b of a base sequence of interest (3) 3 and DNA 4b of a base sequence of interest (4) 4.

FIG. 1(D) is c-probe for detecting the probe DNA hybridized with a sample DNA 5. The c-probe DNA group 15 consist of DNAs 1a to 4a of base sequences of interest (1) to (4) which is in a complementary chain relation to the probe DNA group (8) and are immobilized on glass or membrane 13 to prepare a c-DNA chip 16.

In FIG. 1(E), a sample DNA 5 and a probe DNA group 8 are placed into a hybridization solution 10 and a hybridization is carried out in a tube 19. At that time, when there are base sequences complementary to probe DNAs in a sample DNA 5, the probe DNAs are bonded with sample DNA to form a hybridization complex while non-bonded probe DNAs are remain in a solution. In this example, a complementary chain DNA 1b of a base sequence of interest (1) and a complementary chain DNA 4b of a base sequence of interest (4) are bonded to the sites of a base sequence of interest (1) 1 and a base sequence of interest (4) 4 in a sample DNA 5, respectively.

FIG. 1(F) and FIG. 1(G) show a means for the separation of probe DNAs bonded to a sample DNA 5 from a non-bonded probe DNAs in FIG. 1(E) and the sample DNA 5 is fixed to a magnet 18 as shown in FIG. 1(F) and a solution is transferred from FIG. 1(F) to FIG. (G). At that time, a complementary chain DNA 1b of a base sequence of interest (1) and a complementary chain DNA 4b of a base sequence of interest (4) of probe DNAs bonded to a sample DNA 5 do not move while a complementary chain DNA 2a of a base sequence of interest (2) and a complementary chain DNA 3a of a base sequence of interest (3) of non-bonded probe DNA floating in a solution move as shown in FIG. 1(G). As a result thereof, it is possible to separate the bonded probe DNA and the non-bonded probe DNA whereby the probe DNA bonded to the sample DNA 5 can be selected.

In FIG. 1(H), in order to isolate the bonded probe DNA from the sample DNA, a complementary DNA 1b of a base sequence of interest (1) and a complementary DNA 4b of a base sequence of interest (4) are dissociated from the hybridization complex. The dissociation is carried out by making the solution alkaline or by heating.

In FIG. 1(I) and FIG. 1(J), the sample DNA 5 is separated from the probe DNA and the sample DNA 5 is moved from FIG. 1(H) to FIG. 1(I). By doing so, the probe DNA in FIG. 1(J) is in a solution. It is thus possible to separate the sample DNA 5 from a complementary chain DNA 1b of base sequence of interest (1) and a complementary chain DNA 4b of base sequence of interest (4) of the probe DNA. After that, the separated probe DNA is labeled with a fluorescent substance as shown in FIG. 1(J) for the purpose of reading and, with regard to labeling timing of the fluorescent substance, it may be also carried out at the stage of FIG. 1(C).

In FIG. 1(K), in order to detect the type of the separated probe DNA, the separated probe DNA of FIG. 1(J) and a c-DNA chip 16 of FIG. 1(D) are placed into a hybridization solution 10 and the probe DNAs are hybridized with a c-probe DNA group 15 which is in a relation of complementary chain to the probe DNA. As a result, hybridization complex of DNA 1a of a base sequence of interest (1) with a complementary chain DNA 1b of a base sequence of interest (1) and that of DNA 4a of a base sequence of interest (4) with a complementary chain DNA 4b of a base sequence of interest (4) are formed.

FIG. 1(L) shows detection of a probe DNA forming a hybridization complex in which the c-DNA chip is read by the conventional DNA chip reading device 7.

FIG. 1(M) shows images of read c-DNA chips and, since the position on which the isolated probe DNA is bonded shines, it is now possible to determine which probe DNA is bonded. In this example, it is noted that the probe DNAs of a base sequence of interest (1) and of a base sequence of interest (4) were bonded to sample DNA.

As such, when a probe DNA bonded to a c-DNA chip is determined, it is now possible to detect which base sequence of interest is present in a sample DNA. Although a method of detecting a base sequence utilizing an automated DNA chip for identification of a probe DNA bonded to a sample DNA is illustrated here, any means may be used as a method for identification of a probe DNA bonded to a sample DNA. It goes without saying that a means of the present invention where a probe DNA is detected by a complementary chain probe DNA may also be applied to that which is other than a DNA chip.

As hereunder, an Example where a probe which selectively bonds to a sample DNA of interest is recovered by the above-mentioned method will be shown.

EXAMPLE 1

Hybridization of a Sample DNA to a Probe

As a sample DNA to be detected by the method of the present invention, a DNA which was shown in the SEQ ID NO: 1 was used. Biotin was subjected to a covalent bond at 5'-terminal of the DNA for the purpose of selection after the hybridization. As probes having sequences complementary to the sample DNA, DNAs 1 and 2 of SEQ ID NO: 2 and NO: 3 which have complementary sequences to 20-35 and 41-55 of the DNA sequence of the above sample DNA respectively were chemically synthesized. As DNAs which do not bond to sample DNA, DNAs 3, 4 and 56 of SEQ ID NO: 4, 5 and 6 were used respectively. All of those DNAs including the sample DNA and the probes were mixed and a hybridization was carried out. Condition for the hybridization was that the above DNAs were mixed in a solution containing 5×SSC, 0.5% SDS and 0.2 mg/ml of activated DNA (prepared by a restricted decomposition of DNA of calf thymus with DNase), heated at 95° C. for 3 minutes and allowed to stand at 42° C. for 10 minutes.

Selective Recovery of Probe DNA Bonded to Sample DNA

For the purpose of the present experiment, biotin bonded to the sample DNA was utilized. Biotinylation of DNA can be effected by the methods described in Tetrahedron Letters, 32:1715-1718 and Nucleic Acids Research 20:6253-6259. Biotinylated sample DNA was purchased from Sigma Genosis in this example. Thus, streptavidin specifically bonding to biotin fixed to a magnetic bead (MACS Separation System, Miltenyi Biotech) was used to recover a biotinylated DNA by the following procedures: Thus, a hybridization solution was mixed with 100 μl of MACS Streptavidin MicroBeads and subjected to a column which was set on a strong permanent magnet. The column was previously flown by a solution for hybridization containing no DNA as an equilibrating buffer. To the column into sample was applied, 100 μl of the hybridization solution were flown five times followed by 100 μl TE buffer three times to wash out the DNA bonded thereto in a non-specific manner. The column was then detached from the magnet plate and a TE buffer was flown to recover the sample DNA e bonded to the probe into a tube.

Confirmation for a Selective Recovery of the Probe to the Sample DNA

Figure 3:
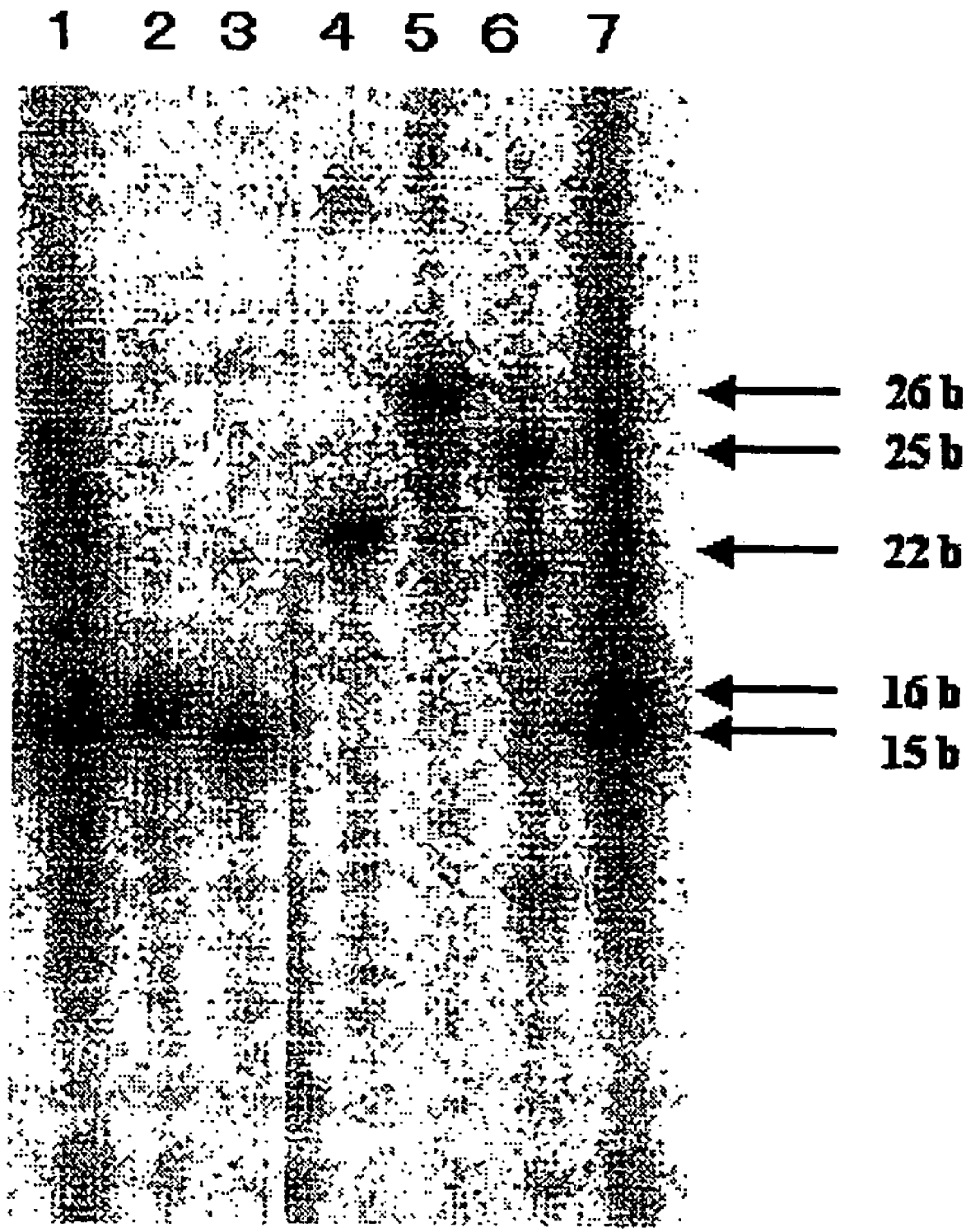
FIG. 3 represents electrophoresis detecting the probe DNA bonded to sample DNA. The DNA solution recovered together with the sample DNA with a magnet method was radioactively labeled and subjected to denatured polyacrylamide electrophoresis. Lanes 1 and 7 were labeled using recovered solution. Lanes 2 to 6 represent electrophoresis using probe DNA (DNAs 1 to 6) radioactively labeled at terminus. lane 2:DNA 1; lane 3:DNA 2; lane 4:DNA 3; lane 5:DNA 4; lane 6:DNA 5.

In order to recover the probe which was bonded to the sample DNA recovered, the DNA solution recovered by TE buffer was treated at 95° C. followed by cooling quickly to dissociate the hybridized DNA and then radioactive [γ $^{32}$P]ATP and polynucleotide kinase were added to the solution to radioactively label the 5'-terminal of probe DNA. The reaction product was subjected to a 20% polyacrylamide gel electrophoresis in the presence of 8M urea and DNA bands were detected by autoradiography. The kind of DNA which had been bonded to the sample DNA was detected by chain length of DNA from the position of the band obtained. That is, if the probe of interest was selectively bonded to the sample DNA and recovered together with the sample DNA by a magnet method, DNAs 1 and 2 were detected as DNA band of 15 and 16 chain length, respectively whereas bands of other chain lengths were not detected. The experimental result exactly came up to the theoretical prediction described above. Thus it showed that the probe having sequences complementary to the sample was specifically bonded to the sample DNA. It is shown from the results of FIG. 3 that plural probe DNAs can bind to one kind sample DNA in equal efficiency, which demonstrate that the principle of the present invention can effectively function.

What is claimed is:

1. A method for the detection of a base sequence of interest in a sample polynucleotide consisting essentially of the steps of:
   (1) contacting the sample polynucleotide with at least one kind of probe polynucleotides in an aqueous solution to form a hybridization complex;
   (2) isolating the hybridization complex;
   (3) dissociating the hybridization complex to recover the probe polynucleotides; and
   (4) identifying the probe polynucleotides to detect the base sequence of interest in the sample polynucleotide;
   wherein each base sequence of interest in the sample polynucleotide is identified by one probe complementary to the base sequence of interest.

2. The method according to claim 1, wherein the hybridization is carried out in such a manner that none of the sample polynucleotide or the probe polynucleotides are immobilized.

3. The method according to claim 1 or 2, wherein plural kinds of probe polynucleotides are used to detect plural base sequences of interest.

4. The method according to claim 1 or 2, wherein the probe polynucleotides are labeled with fluorescent substance.

5. The method according to claim 1 or 2, wherein the probe polynucleotides are identified by means of hybridization with a polynucleotide chain complementary thereto.

6. The method according to claim 5, wherein the polynucleotide chains complementary to the probe polynucleotides are immobilized.

7. The method according to claim 6, wherein the immobilized polynucleotide chain complementary to the probe polynucleotides are in the form of a DNA or RNA chip.

8. The method according to claim 1 or 2, wherein plural kinds of probe polynucleotides are used to detect plural, non-contiguous base sequences of interest.

* * * * *

SEQUENCE LISTING

<160> NUMBER OF SEQ ID NOS: 6

<210> SEQ ID NO 1
<211> LENGTH: 63
<212> TYPE: DNA
<213> ORGANISM: Artificial Sequence
<220> FEATURE:
<223> OTHER INFORMATION: Target Sequence

<400> SEQUENCE: 1
accagaaaaa atttattttt tctggtgttt gccgcccggc tccagtggaa atgaaactct    60
ggg    63

<210> SEQ ID NO 2
<211> LENGTH: 16
<212> TYPE: DNA
<213> ORGANISM: Artificial Sequence
<220> FEATURE:
<223> OTHER INFORMATION: Probe

<400> SEQUENCE: 2
gcggcaaaca ccagaa    16

<210> SEQ ID NO 3
<211> LENGTH: 15
<212> TYPE: DNA
<213> ORGANISM: Artificial Sequence
<220> FEATURE:
<223> OTHER INFORMATION: Probe

<400> SEQUENCE: 3
ttcatttcca ctgga    15

<210> SEQ ID NO 4
<211> LENGTH: 22
<212> TYPE: DNA
<213> ORGANISM: Artificial Sequence
<220> FEATURE:
<223> OTHER INFORMATION: Probe

<400> SEQUENCE: 4
gccaacatat gtcctctgac gc    22

<210> SEQ ID NO 5
<211> LENGTH: 26
<212> TYPE: DNA
<213> ORGANISM: Artificial Sequence
<220> FEATURE:
<223> OTHER INFORMATION: Probe

<400> SEQUENCE: 5
cgcttaaggt tactaacctg tcgagg    26

<210> SEQ ID NO 6
<211> LENGTH: 25
<212> TYPE: DNA
<213> ORGANISM: Artificial Sequence
<220> FEATURE:
<223> OTHER INFORMATION: Probe

<400> SEQUENCE: 6
gcgaacatat ggtcgcctct atcga    25